United States Patent [19]

Zimmerman et al.

[11] E Patent Number: Re. 32,011

[45] Reissued Date of Patent: Oct. 22, 1985

[54] ULTRAPURIFICATION OF FACTOR VIII USING MONOCLONAL ANTIBODIES

[75] Inventors: Theodore S. Zimmerman; Carol A. Fulcher, both of La Jolla, Calif.

[73] Assignee: Scripps Clinic and Research Foundation, La Jolla, Calif.

[21] Appl. No.: 563,795

[22] Filed: Dec. 21, 1983

Related U.S. Patent Documents

Reissue of:

[64] Patent No.: 4,361,509
Issued: Nov. 30, 1982
Appl. No.: 330,105
Filed: Dec. 14, 1981

[51] Int. Cl.[4] ..... C07G 7/00; A61K 35/14

[52] U.S. Cl. ..... 260/112 B; 424/101; 514/8; 514/21

[58] Field of Search ..... 260/112 B; 424/101, 424/177; 514/21.8

[56] References Cited

U.S. PATENT DOCUMENTS

| | | | |
|---|---|---|---|
| 3,631,018 | 12/1971 | Shanbrom et al. | 260/112 B |
| 3,652,530 | 3/1972 | Johnson et al. | 260/112 B |
| 3,682,881 | 8/1972 | Fekete et al. | 260/112 B |
| 3,973,002 | 8/1976 | Hagan et al. | 424/101 |
| 4,069,216 | 1/1978 | Shanbrom | 260/112 B |
| 4,137,223 | 1/1979 | Shanbrom et al. | 260/112 B |
| 4,188,318 | 2/1980 | Shanbrom | 260/112 B |
| 4,203,891 | 5/1980 | Rock | 260/112 B |
| 4,272,521 | 6/1981 | Zuffi | 424/85 |
| 4,296,027 | 10/1981 | Condie | 260/112 B |
| 4,302,445 | 12/1981 | Pla et al. | 424/101 |
| 4,348,315 | 9/1982 | Blombäck et al. | 260/112 B |
| 4,361,510 | 11/1982 | Mitra | 260/112 B |
| 4,361,550 | 11/1982 | Kung et al. | 424/85 |
| 4,361,647 | 11/1982 | Remington | 435/7 |
| 4,362,867 | 12/1982 | Paddock | 536/27 |
| 4,364,861 | 12/1982 | Mitra et al. | 260/112 B |
| 4,364,932 | 12/1982 | Kung et al. | 424/85 |
| 4,364,933 | 12/1982 | Kung et al. | 424/85 |
| 4,364,934 | 12/1982 | Kung et al. | 424/85 |
| 4,364,935 | 12/1982 | Kung et al. | 424/85 |
| 4,364,936 | 12/1982 | Kung et al. | 424/85 |
| 4,364,937 | 12/1982 | Kung et al. | 424/85 |
| 4,373,932 | 2/1983 | Gribnau et al. | 436/501 |
| 4,376,110 | 3/1983 | David et al. | 436/513 |
| 4,381,292 | 4/1983 | Bieber et al. | 424/1 |
| 4,381,295 | 4/1983 | Kung | 424/85 |

FOREIGN PATENT DOCUMENTS 0038642 10/1981 European Pat. Off. .

OTHER PUBLICATIONS

Muller et al., Blood, vol. 58, No. 5, pp. 1000–1006, Nov. 1981.
J. Nara Med. Ass. 30, 199–212 (1979), Fujimura.
Annal N.Y. Acad. Sci. 370, 210–226, (1981), McKee.
Monoclonal Antibodies, Scientific American 243:66–74 (Oct. 1980), Milstein.
Eur. J. Immunol., 9:155–159 (1979), Sunderland et al.
Monoclonal Antibodies, Plenum Press, New York, 1980 (Text), pp. 395–397, Kennett et al.
Blood 58, 1 (1981), Hoyer.
J. Biol. Chem., 248, 3946 (1973), Legaz et al.
J. Lab. Clin. Med. 77, 185 (1971), Hershgold et al.
Proc. Natl. Acad. Sci. USA, 79, 7200 (1982), Fay et al.
Blood, 63, No. 2, 486–489 (1984), Fulcher et al.
J. Clin. Invest., 73(2), 307–16 (1984), Weinstein et al.
Progress in Hematology, 13, 279 (1983), Zimmerman et al.
J. Lab. Clin. Med., 736–746 (May 1983), Rotblat et al.
Journal of Immunology, 128, No. 6, 2709–2713 (Jun. 1982), Ehrlich et al.
J. of Immunol. Methods, 39, 285–286, 307–308 (1980), Goding.
Thrombosis Research, 13, No. 3, 409–418 (1978), Lavergne et al.
Thrombosis Research, 8, 777–783 (1976), Brown et al.
J. of Lab. Clin. Med. vol. 93 p. 40 (1979), Tuddenham et al.
British J. of Hematology vol. 43 p. 669 (1979), D. E. G. Austen.
Immunoassays: Clinical Lab. Tech. For The 1980's, R. M. Nakamura et al. Eds. pp. 339–349 (1980), Zimmerman et al.
Journal of Bio. Chemistry, vol. 225, pp. 4980–4983 (1980), J. P. Brown et al.
Journal of Chromatography, vol. 86, pp. 53–56 (1973), J. Porath et al.
Proc. Natl. Acad. Sci. USA, vol. 78, No. 1, p. 162 (1/1981), J. A. Katzman.
British J. of Hematology, vol. 40, p. 631 (1978), J. M. Lavergne et al.
Thrombosis Research, vol. 12, p. 667 (1978), L. Holmberg et al.
Abstracts Circulation, vol. 62, Supp. III, (10/80) No. 648, J. A. Katzman et al.
British Journal Cancer, vol. 40 p. 701 (1979), S. Pahlman et al.
Journal of Bio-Chemistry, vol. 254, p. 8709 (1979), P. Parham.
Proc. Natl. Acad. Sci. U.S.A., vol. 77, No. 12, p. 7034, (1980) C. M. Fraser.

(List continued on next page.)

*Primary Examiner*—Howard E. Schain
*Attorney, Agent, or Firm*—Eugene Moroz; William S. Feiler

[57] ABSTRACT

A method of preparing high purity procoagulant protein comprising the steps of (a) adsorbing a VIII:C-/VIII:RP complex from a plasma or commercial concentrate source of factor VIII onto agarose beads bound to a monoclonal antibody specific to VIII:RP, (b) eluting VIII:C with a salt solution, (c) adsorbing the eluted VIII:C on an animohexyl agarose column and eluting the VIII:C with a salt solution.

36 Claims, No Drawings

OTHER PUBLICATIONS

Clin. Exp. Immunology, vol. 42, p. 458 (1980), M. Shigeta et al.
C.R. Acad. Science Paris t. 293 p. 447 (2 Nov. 1981), N. Josso et al.
Arch. Geschwulstforsch, vol. 51/4 p. 302 (1981), M. R. Price et al.
Proc. Natl. Acad. Sci. USA, vol. 76 p. 1420 (1979), J. Sharon et al.
Immunology, vol. 35, p. 429 (1978), G. N. Abraham.
Immunology, vol. 31, p. 893 (1976), M. O. Bubb et al.
Journal of Immunological Methods, vol. 38, p. 239 (1980), W. Romer et al.
Journal of Steroid Biochemistry, vol. 15 p. 131 (1981), H. R. Linder et al.
Biochemistry, vol. 20, No. 19, p. 5625 (1981), J. S. Pober et al.
Analytical Biochemistry, 111 p. 1 (1981), G. S. Eisenbarth.
Ann. Rev. Biochemistry 1981, vol. 50, p. 657, D. E. Yelton et al.
Clinics In Hematology, vol. 8, No. 1, p. 207 (1979), S. Shapiro.
C. R. Seances Acd. Sci. III (France) Abstract, vol. 293 (8) p. 447 (1981), N. Josso et al.
Clinical Exp. Immunology Abstract vol. 33 (3) p. 425 (1978), D. G. Williams.
J. Immunogenet, Abstract, vol. 4 (4) p. 233 (1977), J. M. Moseley et al.
VOPR Virasol, O (2) p. 136 (1981), M. A. Yakhno et al.
J. Immunol Abstract, vol. 127 (6) p. 2580 (1981), B. K. Seon.
J. Bio-Chemistry Abstract, vol. 256 (9) p. 4433 (1981), D. M. Kranz et al.
Fed. Proc. U.S.A. Abstract vol. 40/31 (99) (1981), C. M. Fraser et al.
J. Steroid Bio-chemistry Abstract, vol. 15/1 (131-136), H. R. Lindner et al.
Rev. Med. Interne Abstract, vol. 2/4 (425-429) (1981), Y. Chestier et al.
Mol. Immunol Abstract, vol. 18/9 p. 831 (1981), J. Sharon et al.
Scand. J. Immunol. Abstract, vol. 11/1 p. 37 (1980), E. B. Myhre.
Journal of Clinical Investigation, vol. 50, No. 1, pp. 244-254, (Jan. 1971), Zimmerman et al.
Journal of Experimental Medicine, 138, No. 4, pp. 1015-1020, (1973), Zimmerman et al.
Symposium VIII, Factor VIII/von Willebrand Factor, Abstract No. 0476, Jul. 14, 1981, Fass et al.
Abstracts Circulation, vol. 66, Supp. II, Oct. 1982, Fay et al.
Biochemistry, vol. 19, No. 3, Feb. 5, 1980, Vehar et al.
Biochimica et Biophysica Acta, 668, pp. 471-480 (1981), Harris et al.
Biochimica et Biophysica Acta, 668, pp. 456-470, (1981), Harris et al.
Thromb. Haemost, Abstract 0506, vol. 46, p. 166 (7/12/81), Bowie et al.
Fed. Proc., Abstract 3430, vol. 40, p. 3 (1981), Katzman et al.
Thromb. Haemost, Abstract 0505, vol. 46, p. 165 (7/12/81), Fass et al.
Blood, vol. 58, pp. 530-535 (1981), Katzman et al.
Blood, vol. 59, pp. 594-600 (1982), Fass et al.
Symposium on Factor VIII, Abstract/Presentation, (10/7-9/82), Katzman et al.
Thromb. Haemost., Abstract 0261, vol. 46, p. 88, (7/12/81), Katzman et al.
Methods Enzymol, vol. 80, pp. 249-274 (1981), Nesheim et al.
Thrombosis Research, vol. 20, pp. 85-96 (1980), Muller et al.
Blood, vol. 59, No. 3 (3/1982), Goodall et al.
"Hybridoma Antibody Analysis of Molecular Biology of Coagulation Proteins", 34th An. Mt. A.A. Blood Banks (11/3/81), Edgington et al.
Blood, vol. 61, No. 1 (1/83), Ogata et al.
Blood, vol. 59, No. 3, (3/82), Knutson et al.
J. Lab. Clin. Med., vol. 89, No. 6, pp. 1295-1305 (6/77), Brockway et al.
Science, vol. 222, pp. 721-726 (11/18/83), Teillaud et al.
Proc. Natl. Acad. Sci. U.S.A., vol. 79, pp. 1648-1652, Mar. 1982.

ULTRAPURIFICATION OF FACTOR VIII USING MONOCLONAL ANTIBODIES

Matter enclosed in heavy brackets [ ] appears in the original patent but forms no part of this reissue specification; matter printed in italics indicates the additions made by reissue.

*The invention described herein was made in the course of work under a grant or award from The Department of Health, Education and Welfare and the Government has certain rights therein.*

BACKGROUND OF THE INVENTION

1. Field of the Invention

This invention relates generally to a method of separating and purifying factor VIII procoagulant activity protein. More specifically, high purity factor VIII procoagulant activity protein is separated from von Willebrand Factor by a two step chromatographic adsorption and concentration technique from plasma or concentrate.

2. Description of the Prior Art

The isolation of the antihemophilic factor from blood plasma has been described in the literature. The precise structure of the antihemophilic factor, also referred to as factor VIII procoagulant activity protein (factor VIII), has not yet been identified, due in part to the unavailability of sufficient quantities of pure material with which to conduct further studies. The limited availability of pure material and its existence in a dilute state has also hindered its use in therapeutic applications.

Factor VIII procoagulant activity protein functions to correct the clotting defect in hemophilic plasma. It circulates in plasma complexed with the von Willebrand factor protein. The latter can alter the platelet function defect in von Willebrand's disease. That portion of the factor VIII von Willebrand factor complex having coagulant activity is referred to as factor VIII procoagulant activity protein, factor VIII-clotting activity or simply VIII:C (the designation of "VIII:C" will be used hereinafter to identify the portion of the factor VIII molecule with such clotting activity.) The other portion of the factor VIII von Willebrand factor complex having the ability to correct the platelet function defect in von Willebrand's disease is referred to as von Willebrand factor, factor VIII-related antigen, VIIIR:Ag, VIII:RP factor. (The description "VIII:RP" will be used hereinafter to identify the platelet correction function of the factor VIII molecule). Although yet unproven, there is evidence to support the conclusion that VIII:C exhibits properties and the behavior of a small molecule which is combined with VIII:RP as a non-covalent complex. There is also a basis for the contention that the properties associated with both VIII:C and VIII:RP may also be a single molecule which under appropriate conditions may be cleaved, yielding two fragments.

In view of the need for identifying the structures of the factor VIII/von Willebrand factor complex, VIII:C and VIII:RP and the important pharmaceutical value of the coagulant activity ascribable to VIII:C, numerous attempts have been made to purify factor VIII and to separate and concentrate VIII:C and VIII:RP. The techniques used are based generally on either immunoadsorption or ion exchange chromatography.

Such techniques as heretofore used have had limited success due to the difficulty of desorbing the proteins from the charged ionic material in an undamanged condition or recovering same in suitable quantities.

One such method for separating VIII:C from VIII:RP utilizing immunoadsorbent chromatography has been reported by E. G. D. Tuddenham et al, "The Properties of Factor VIII Coagulant Activity Prepared by Immunoadsorbent Chromatography", JOURNAL OF LABORATORY CLINICAL MEDICINE, Vol. 93, p. 40 (1979). The reported method is a one-step separation of VIII:C from nearly all VIII:RP and from most other plasma proteins employing a chromatographic column packed with agarose beads to which polyclonal antisera to VIII:RP (anti-VIII:RP) are coupled. Factor VIII/von Willebrand factor containing plasma is passed through the column which adsorbs both VIII:C and VIII:RP. Other unwanted plasma proteins are removed from the column by washing with buffered saline solution and the desired VIII:C is obtained by subsequent elution with a calcium-ion gradient. Although it is stated to be an improvement in both purity and yield of VIII:C, when compared to the previously known methods, it is also stated that the resulting product also contains VIII:RP and other plasma proteins. Such contaminants may be attributable to the use of polyclonal antisera bound to the agarose beads. Since a majority of the immunoglobulins from which the antisera are constituted are not specific to VIII:RP, the effective number of sites where antibodies specific to VIII:RP may be bound to agarose is relatively small due to competition between the antisera for a finite number of bonding sites on the agarose.

Another method for separating VIII:C from VIII:RP and ristocetin co-factor by a chromatographic technique employing aminohexyl-substituted agarose has been described by D. E. G. Austen, "The Chromatographic Separation of Factor VIII on Aminohexyl Sepharose," BRITISH JOURNAL OF HAEMATOLOGY, Vol. 43, p. 669 (1979). The described method is stated to be an improved method for the component parts of both human and porcine factor VIII/von Willebrand factor. This method, however, also suffers from the fact that contaminants are present in the resulting product. In both the Tuddenham et al and Austen methods a contaminated product, which is more dilute than is normally desired, is formed.

Hence, it is clear that there still exists a need for an improved method for separating and purifying VIII:C from VIII:RP using plasma or concentrates. Therefore, it is an object of the present invention to satisfy such a need.

SUMMARY OF THE INVENTION

The present invention relates to a method of separation of the component molecules of the factor VIII/von Willebrand factor complex, VIII:C and VIII:RP, and the purification and concentration of the pro-coagulant activity protein VIII:C. The method achieves the object of producing highly purified VIII:C using a two step procedure.

The first step involves immunoadsorption of factor VIII from plasma or a commercial concentrate. The adsorbent employed comprises a monoclonal antibody specific to VIII:RP which is bound to a suitable substrate such as, agarose beads. After the VIII:C/VIII:RP is initially adsorbed, the substrate particles are washed extensively with a buffer solution to remove unadsorbed protein. The adsorbed material is then treated with a calcium ion containing solution to elute the adsorbed VIII:C. The VIII:RP portion remains adsorbed on the anti-VIII:RP bound material. At this point about 40–60% of the VIII:C initially adsorbed is recovered in a highly purified state. However, the procoagulant activity protein recovered, although extremely pure, i.e., largely free from contaminants, is too dilute to be of significant therapeutic value.

The second step of the present process is directed to substantially concentrating the recovered purified VIII:C using a technique which may be characterized as affinity chromatography.

The VIII:C solution obtained from the first step of the present process having a potency of approximately 10–20 International Units (hereinafter "units") is processed in a column containing aminohexyl substituted agarose. The column is then washed with a buffer solution and the VIII:C is eluted with a calcium ion-containing solution to yield a VIII:C concentration in excess of 1000 units per ml, and being greater than 160,000 fold purified from plasma. Thus, the present method yields unexpectedly high purity procoagulant activity protein in a highly concentrated and therapeutically useful state. Methods used heretofore fail to achieve such notable results for several reasons. The method of Tuddenham et al, described earlier, employs bound polyclonal antisera instead of the specific and highly selective monoclonal antibodies to VIII:RP as used in the present invention. As a result, fewer specific antibodies to VIII:RP are coupled for a given weight of agarose. In the method of the present invention monoclonal antibodies are exclusively bound to a relatively inert substrate. When the method of Tuddenham et al is used only 2.6 to 6.4 units of VIII:RP per ml of immunoglobulin-agarose beads (equivalent to 53.1–82.9% of the amount applied to the column) are removed. This compares to greater than [1,000] *12.5–18.8* units per ml of beads (or 90–100% of the VIII:RP which is applied to the column) which is recovered when the monoclonal antibody immunoadsorbent of the present invention is employed. This ability to adsorb more VIII:C/VIII:RP (factor VIII/von Willebrand factor) per ml of beads accordingly results in a higher concentration of VIII:C when it is subsequently eluted from the immunoadsorbent. Thus, 10–20 units of VIII:C per ml of eluant are obtained with the present invention, in contract to 0.5–1.25 units per ml of eluant with the Tuddenham et al method.

The present method also permits the selection of a monoclonal antibody having a high affinity for VIII:RP; however, the use of polyclonal antibodies results in varying affinities. It should be realized that there is an indirect relationship between the affinity of the bound antibody for VIII:RP and the elution of VIII:RP. Thus, the higher the affinity of the antibody for VIII:RP, the less VIII:RP will be present with VIII:C in the eluant. The present invention also makes it possible to produce an unlimited supply of the specified monoclonal antibody, thus eliminating variations among different batches.

Although Austen, as earlier described, has reported the use of aminohexyl-agarose to separate VIII:C from VIII:RP, such a material has not heretofore been used to concentrate VIII:C following a separation and purification step. Heretofore, the highest VIII:C concentrations achieved by using aminohexyl agarose in chromatography were 0.53 units per ml of eluant for human protein and 2.38 per ml of eluant for porcine VIII:C. The present method permits concentrations several orders of magnitude greater than these. Perhaps of even greater significance, is the fact that the present invention provides for a greater purification of human VIII:C than has ever been reported (164,000 vs 17,000 fold over plasma). The present method, which is described in more detail hereinafter, yields VIII:C with a specific activity of 2,300 units/mg when commercial concentrate is used. This corresponds to a 164,000 fold purification from plasma. The ratio of VIII:C to VIII:RP is greater than $10^5$ as compared to the ratio in plasma.

DESCRIPTION OF THE PREFERRED EMBODIMENTS

The following description provides details of the manner in which the embodiments of the present invention may be made and used in order to achieve the separation, purification and concentration of VIII:C to a degree of purity and concentration not known heretofore. This description, while exemplary of the present invention, is not to be construed as specifically limiting the invention and such variations which would be within the purview of one skilled in this art are to be considered to fall within the scope of this invention.

A. Preparation of Monoclonal Antibody to VIII:RP

The monoclonal antibody to VIII:RP which is subsequently bound to the separation substrate may be prepared in a stepwise procedure starting with a highly purified preparation of factor VIII/von Willebrand factor (VIII:C/VIII:RP complex). The purification for immunization is accomplished with material obtained from a plasma source. Less highly purified material for coating polyvinyl plates is obtained in higher concentration from commercial extracts such as FACTORATE (trademark of Armour Pharmaceutical Co., Tuckahoe, N.Y.) or Hemophil (trademark of Hyland Laboratories, Costa Mesa, California). Purification is performed by a standard agarose-gel filtration of cryoprecipitate, such as that described by Zimmerman and Roberts, "Factor VIII Related Antigen", appearing in IMMUNOASSAYS: CLINICAL LABORATORY TECHNIQUES FOR THE 1980's, R. M. Nakamura et al, eds., Alan R. Liss, Inc., New York, pp. 339–349 (1980). Mice were injected with highly purified factor VIII/von Willebrand factor obtained from plasma according to the following procedure. On day zero, the mice are injected intraperitoneally with a composition prepared by dissolving (or suspending) 10 Mg of the protein in 0.1 ml of buffer containing 0.05 M Tris, 0.15 M sodium chloride, 0.02% sodium azide, 1 mM phenyl methyl sulfonyl fluoride, traysylol 10 units/ml at pH7.3. and shaking with an equal volume of complete Freund's adjuvant. On day 14, the mice are again injected with the same material except that incomplete Freund's adjuvant is substituted for complete Freund's adjuvant. On day 21, the injection of day 14 is repeated. On day 38, the mice are injected with purified VIII:C/VIII:RP only. On day 42, the spleens of the mice are removed and fused according to a standard procedure, of the type described by J. P. Brown et al "Protein Antigens of Normal and Malignant Human Cells Identified by Immunoprecipitation with Monoclonal Antibodies", JOURNAL OF BIOLOGICAL CHEMISTRY, Vol. 225, pp. 4980–4983 (1980). The standard technique is varied only to the extent that 35% polyethylene glycol 1000 is substituted for 50% polyethylene glycol. A radioimmunoassay method for clones producing antibody to VIII:RP is performed according to the following procedure. Polyvinyl plates with a "V" bottom, flexible type are coated with 0.1 ml of factor VIII purified from commercial extract according to the procedure indicated above and having a concentration of 0.125 mg/ml of protein. The plates are blocked with albumin, washed with buffer and incubated with the culture fluids from the clones to be tested. The plates are then washed and reacted with rabbit anti-mouse IgG antiserum, washed a second time and $^{125}I$ labeled goat anti-rabbit IgG antiserum is added to the wells and incubated. The plates are again washed, then dried and the wells cut-out and counted. After determining the clones which are positive they are subcloned at least twice and stable clones producing antibody to VIII:RP are then injected into the peritoneal cavities of Balb/C mice which have been pretreated intraperitoneally with 0.5 ml of pristane at least four days prior to injection of cells. Hybridoma cells are injected at concentrations of approximately $5\times10^6$ cells per mouse in 0.5 ml of Delbecco's modified Eagle's medium without fetal bovine serum. The mice are tapped when bloated and ascites fluid is collected in heparin at approximately 10 units/ml. Ascites fluid from multiple mice is pooled to provide a convenient volume for subsequent isolation of the monoclonal IgG. If the heparinized ascites fluid is not used immediately, it may be stored at −70° C. and thawed just prior to use. The final yield of IgG from the ascites fluid is approximately 1 g of IgG per 100 ml of ascites fluid.

The specificity of the monoclonal IgG for the purpose of purifying VIII:C may be assessed by coupling the IgG to a separation substrate medium, in the manner described hereinafter, and demonstrating that the bound IgG removes from VIII:RP and VIII:C from plasma and that the VIII:C may be subsequently eluted with a solution containing calcium ions while the VIII:RP remains complexed to the monoclonal IgG which is bound to the solid-state substrate.

The monoclonal IgG, which is to be used subsequently to prepare the immunoadsorbent, may be isolated from heparinized pooled ascites fluid immediately after collection or a frozen portion of the stored solution may be thawed. Regardless of whether fresh or frozen material is used, the solution is brought to 4° C. and treated with an equal volume of phosphate buffered saline solution (PBS), the composition of which is set forth below. The diluted ascites is precipitated by dropwise addition with stirring at 4° C. of an equal volume of saturated ammonium sulfate (SAS); prepared by boiling an excess of ammonium sulfate in water, cooling to 4° C., filtering undissolved crystals and adjusting the pH to 7.0 with ammonium hydroxide. The precipitate and its supernatant liquid are stirred for at least 2 hours and centrifuged at 4° C. Centrifugations are preferably carried out at 14,000 rpm for 60 minutes (30,000×g). The supernatant solution of ascites is precipitated twice more with SAS and the mixture of precipitate and supernatant liquid stirred and centrifuged in the same manner as in the first cycle. The pellets resulting from the third precipitation are resuspended in a volume of PBS equal to that of the diluted ascites fluid and then disalyzed exhaustively against PBS. Clots appearing in the dialysis bags are removed by centrifugation at 20° C. The dialyzed IgG is adsorbed by stirring it with a 5% aqueous solution of aluminum hydroxide at room temperature and centrifuging at 20° C. after adsorption. The adsorption treatment is repeated at least three more times using 2.5% aluminum hydroxide solution for each treatment after the first. The adsorbed IgG is brought to 4° C. and reprecipitated once with SAS as described above. The precipitated pellets may be stored at −20° C. until used.

B. Preparation of the Immunoadsorbent

The immunoadsorbent is prepared by suitably preparing the monoclonal IgG for coupling, preparing the solid substrate for coupling and reacting the two components to bind the former to the later.

(i) Preparation of IgG for Coupling

Either freshly precipitated IgG may be used or previously frozen precipitate may be thawed for use. The material is then dialyzed against PBS, and while still in the PBS, the volume and IgG concentration ($A_{280}/1.4$=mg/ml IgG) are determined. The IgG is then treated with between 10 and 30 microliters, preferably 20 microliters, or diisopropylfluorophosphate per 50 ml of IgG solution. The resulting solution is stirred at room temperature in a hood for 30 minutes and the treated IgG, immediately prior to use, is dialyzed overnight against coupling buffer. The coupling buffer found most suitable is a 0.25 M sodium bicarbonate solution adjusted to a pH of 9, preferably with sodium hydroxide.

(ii) Preparation of Solid Substrate for Coupling

Although the monoclonal antibody may be bound to any material which does not have a high affinity for protein, particularly factor VIII itself, such materials as glass beads, agarose and derivatives thereof are preferred. Most preferred is a crosslinked agarose available commercially as a gel known as Sepharose CL2B (trademark of Pharmacia Fine Chemicals, Piscataway, N.J.).

The method of preparing the preferred immunoadsorbent resin is generally the same as that disclosed in the literature, such as the method of J. Porath et al, JOURNAL OF CHROMATOGRAPHY, Vol. 86, pp. 53–56 (1973). The method found most suitable is as follows: a volume of about 2 liters of Sepharose CL2B is placed in an acid-cleaned 2 liter sintered glass filter funnel. The resin is washed with water and filtered to a moist cake. The washed resin is placed in a large (approximately 4 liter) glass beaker equipped with a magnetic stirring bar. To the resin is then added 750 ml of cold potassium phosphate buffer solution, prepared by mixing one part of a 5 M dibasic potassium phosphate solution with two parts of 5 M tribasic potassium phosphate solution. Sufficient cold water is added to bring the final volume to 3 liters. The mixture is then chilled to 4° C. and maintained at between 4°–10° C. in an ice-water bath placed on a magnetic stirring plate. In a hood, cyanogen bromide is added to 300 ml of water in a stoppered glass bottle containing a magnetic stirring bar. The mixture is rapidly stirred until solution results. The cyanogen bromide solution is then added with stirring over a 2 minute period to the cold Sepharose mixture. Stirring is continued for an additional 8 minutes and then transferred to a chilled 2 liter sintered glass filter funnel supported in a 4 liter vacuum flask. The cyanogen bromide treated resin is then washed with approximately 20 liters of cold water or until the pH of the filtrate is neutral. The washed resin is then quickly equilibrated with cold coupling buffer and then transferred to a 4 liter plastic beaker equipped with a large magnetic stirring bar.

(iii) Coupling the Monoclonal Antibody to the Solid Substrate

The solid substrate resin, prepared as indicated above, is ready to be used when it is equilbrated with coupling buffer and should not be stored thereafter. Accordingly, the resin mixture is combined with the IgG which was previously dialyzed overnight against coupling buffer. The combined resin/IgG suspended mixture is stirred at 4° C. for a period of about 24 hours. The $A_{280}$ of an undiluted sample of the supernatant coupling liquid may be determined using bovine serum albumin (BSA) as a standard or Bio-Rad protein assay (Bradford reagent) with BSA as standard. The percentage ligand which is coupled may then be calculated. When the above described procedure is followed, this is usually about 95%. Any remaining active sites on the resin not coupled to antibody may be blocked by washing the resin on a sintered glass filter funnel with cold coupling buffer containing 0.1 M glycine. The resin is then resuspended in this solution to a final volume equal to that when the resin and antibody, each in coupling buffer, were combined. The suspension is stirred slowly overnight at 4° C. The resin is then washed thoroughly with VIII:C-buffer, the composition of which is given below. The coupled, blocked resin is then pre-eluted with VIII:C-buffer additionally containing 0.5 M calcium ions, preferably calcium chloride. The resin is again washed with VIII:C buffer alone and stored at 4° C. or in a continuously pumped column at room temperature until ready for use. The coupling density of IgG to SEPHAROSE should be 2–5 g, preferably 3–4 g IgG/liter of SEPHAROSE.

C. Separation and Purification of VIII:C (i) Sample preparation of factor VIII, such as human and animal plasmas and commercial concentrates of factor VIII, may be employed in the present invention and the method is not limited as to a particular type of material. Preferred materials, and those which have demonstrated successful results, are porcine and human plasmas and commercially available concentrates of human factor VIII, such as FACTORATE available from Armour Pharmaceutical Co. The following description provides details for using both porcine plasma or commercial human concentrate such as FACTORATE:

FACTORATE is reconstituted by adding 25 ml portions of VIII:C-buffer to the contents of each of 20 bottles containing 400–500 VIIIC units per bottle (25 ml per bottle). The mixture is adjusted to a final volume of 1 liter with VIII:C-buffer. A sample aliquot of 0.5 ml may be removed for assay and the remaining material applied to the immunoadsorbent column overnight at a rate of approximately 60 ml/hour.

Porcine plasma, when not freshly drawn, is citrated by conventional means and stored frozen. When ready to be used it is thawed at a temperature of between 35°–40° C., preferably 37° C. and applied directly to the column at 60 ml/hour.

It should be noted that while the description of the present invention refers, and is directed primarily, to the use of immunoadsorbent coupled particles in a chromatography column, it is within the scope of this invention to perform batchwise separations by placing the antibody-bound resin particles in a suitable container and after adding reconstituted concentrate or plasma, VIII:C as outlined above and described in more detail below.

When the process is carried out in a chromatography process, the following embodiments are preferred:

The resin is placed in a column, such as an Amicon 86001, (trademark of Amicon Corp., Lexington, Mass.), equipped with a peristaltic pump and a high flow head. When concentrate is used as the source of factor VIII, for 20 bottles of diluted concentrate, approximately 1.5 liters of resin, prepared as indicated above, is used. When porcine plasma is used, 150 ml of resin is used for each liter of plasma.

After the sample is applied to the column, it is washed with 1 liter of VIII:C-buffer, followed by a second washing with VIII:C-buffer which additionally contains 0.5 M NaCl. Approximately 20 liters of saline-buffer is used when factor VIII is applied as concentrate and 20 bed volumes when porcine plasma is employed. Optimum results are obtained with a flow rate of 1 liter/hour.

Elution of purified VIII:C is accomplished with VIII:C-buffer containing calcium ions. Although a linear gradient, as taught by Tuddenham et al, supra, works well, it is not required in order to accomplish the object of this invention; a solution having a fixed calcium ion concentration is quite adequate. Thus, when VIII:C derived from concentrate is being eluted, VIII:C-buffer, 0.25 to 0.5 M with respect to calcium chloride, preferably 0.35 M, is used advantageously as a flow rate of between 450 to 750 ml/hour and preferably 600 ml/hour. When the VIII:C is obtained from porcine plasma, elution is performed with VIII:C-buffer being a calcium chloride concentration of between 0.35 and 0.7 M, preferably 0.5 M and at a flow rate of between 10 and 30 ml/hour, preferably 20 ml/hour. Fractions of 12 ml and 3 ml are collected for VIII:C originating from concentrate and porcine plasma, respectively. Those fractions containing at least 1.0 unit/ml of VIII:C activity are pooled and the total volume and activity of the pool determined.

The VIII:C pool is initially concentrated to 10–20 ml by a standard procedure such as pressure ultrafiltration. For this purpose, Amicon stirred cell in which a YM-10 membrane under 50 psi of nitrogen pressure has been found to work well. Slow stirring is continued for 30 minutes after nitrogen pressure is released, and the volume and activity of the concentrated pool are determined. The pool may be stored for a brief period, that is, overnight for example, if a temperature of 4° C. is maintained.

It may be noted that the immunoadsorbent column described above may be regenerated by treatment of the column with 2 bed volumes of 3 M aqueous sodium thiocyanate solution run at a flow rate of about 0.5–1 liter/hour to elute VIII:RP.

D. Concentration of Purified VIII:C

Although the VIII:C recovered from the separation from VIII:RP by means of the immunoadsorbent column is highly purified, it is still too dilute to be therapeutically useful. Further concentration and a four fold increase in purification when porcine plasma is used is accomplished by use of an aminohexyl agarose column which is prepared and used in the following manner:

(i) Preparation and/or Conditioning of a Aminohexyl Agarose Column:

Aminohexyl agarose is agarose which has been reacted with 1,6-diaminohexane to yield an agarose resin having a number of 6 carbon atom chains, each of which has a terminal amino group. It may be prepared according to the method described by Austen, supra, or acquired from a commercial supplier. One such material which has been used successfully in the present invention is available under the name of AH-SEPHAROSE 4B (trademark of Pharmacia Fine Chemicals, Piscataway, N.J.).

Whether prepared or purchased, the resin should be conditioned prior to use. This may be accomplished as follows, the volumes, amounts and dimensions being adjusted in proportion to the amount of material to be concentrated:

Approximately 1 gram of aminohexyl agarose (AH-SEPHAROSE 4B) is placed in a sintered glass filter funnel and washed with at least 200 ml of 0.5 M sodium chloride, while stirring. The resin is then equilibrated with VIII:C-buffer and packed in a column of approximately 0.9 cm diameter. A Bio-Rad Econo-Column with flow adapters has proven quite suitable for the type of use considered here. The bed volume of the packed column is approximately 4 ml.

(ii) Application to and Use of the Aminohexyl Agarose Column

The concentrated pool, prepared as described above, is diluted 1:10 in VIII:C-buffer to a final concentration of 100–200 ml when using the amounts of resin and column size as described in the immediately preceding section. The diluted pool is applied to the column at a flow rate of 200 ml/hour.

The column is then washed with VIII:C-buffer which contains calcium ions, preferably from calcium chloride. The solution should be between 0.01 M to 0.03 M, preferably 0.025 M with respect to calcium ions.

Elution of the concentrated VIII:C is achieved at a flow rate of between 5 to 20 ml/hour, preferably 10 ml/hour with VIII:C-buffer containing a higher concentration of calcium ions than was employed with the preceding washing step. Again, calcium chloride is the preferred source of calcium ions in a concentration of between 0.25 to 0.5 M, preferably 0.3 M. Fractions of 1 ml volume are collected and assayed as described below. Collected fractions may be stored at 4° C. or frozen. Preparations of VIII:C obtained from a porcine plasma source should be stabilized within 5 to 10% human serum albumin prior to storage.

Assays may be performed by diluting the fractions with VIII-C buffer if necessary and further diluting the fraction 1:100 in assay buffer prior to addition to the substrate. A standard partial thromboplastin time assay is employed.

The composition of the buffer solutions is as follows:

Phosphate Buffered Saline Solution:

1.6 g sodium phosphate, monobasic monohydrate
8.4 g sodium phosphate, dibasic anhydrous
61.4 sodium chloride
Water to 7 liters
pH of buffer is 7.2

VIII:C-Buffer ml 0.02 M imidazole
ml 0.15 M sodium chloride
ml 0.10 M lysine
ml 0.02% sodium azide pH of buffer is adjusted with concentrated hydrochloric acid to 6.8.

The data listed hereinafter in Tables I and II are representative of that obtained according to the present invention, as described above.

TABLE I

VIII:C Obtained From FACTORATE Concentrate as the Source of VIII:C/VIII:RP

| | Volume (ml) | VIIIC (Units/ml)* | VIIIC (Total Units) | Protein (mg/ml) | Protein (Total mg) | Recovery (%) | Specific Activity (Units/mg) | From Plasma (Fold Purif.) |
|---|---|---|---|---|---|---|---|---|
| Sample Applied to Immunoadsorbent | 500 | 18.8 | 9400 | 29 | 14.500 | — | 0.7 | 50 |
| Pool resulting from Immunoadsorbent | 1020 | 4.6 | 4692 | — | — | 50 | — | — |
| Pool After Initial Concentration | 20 | 134 | 2680 | — | — | 29(57) | — | — |
| Sum Resulting from Aminohexyl Column | — | — | 1576 | — | — | 17(59) | — | — |
| Aminohexyl Fraction #3 | 0.95 | 1172 | 1112 | 0.51 | 0.48 | 12 | 2294 | 163.857 |
| Aminohexyl Fraction #4 | — | 545 | — | 0.23 | — | — | 2370 | 169.285 |

*A frozen human plasma pool used as the standard for VIIIC assays and assigned the value of 1 human unit per ml.

TABLE II

VIII:C Obtained From Citrated Porcine Plasma

| | Volume (ml) | VIIIC (Units/ml) | VIIIC (Total Units) | Protein (mg/ml) | Protein (Total mg) | Recovery (%) | Specific Activity (Units/mg) | From Plasma (Fold Purif.) |
|---|---|---|---|---|---|---|---|---|
| Sample Applied to Immunoadsorbent | 1000 | 1* | 1000 | 76 | 76.000 | 100 | 0.013 | — |
| Pool Resulting from Immunoadsorbent | 70 | 8.8 | 613 | — | — | 61 | — | — |
| Pool After Initial Concentration | 5.76 | 88 | 494.5 | 0.242 | 1.355 | 49.5 | 364 | 28.000 |
| Sum Resulting from Aminohexyl Column | 5.0 | 49 | 247 | 0.035 | 0.175 | 25 | 1413 | 109.000 |

*Porcine plasma used as the standard for VIIIC assays and assigned the value of 1 porcine VIIIC unit per ml.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. An improved method of preparing Factor VIII procoagulant activity protein comprising the steps of (a) adsorbing a VIII:C/VIII:RP complex from a plasma or commercial concentrate source onto particles bound to a monoclonal antibody specific to VIII:RP, (b) eluting the VIII:C, (c) adsorbing the VIII:C obtained in step (b) in another adsorption to concentrate and further purify same, (d) eluting the adsorbed VIII:C, and (e) recovering highly purified and concentrated VIII:C.

2. A method according to claim 1, wherein the elutant used in each of steps (b) and (d) is a saline solution.

3. The method according to claim 2, wherein the saline solution is calcium chloride.

4. The method according to claim 3, wherein the concentration of said calcium chloride solution used in steps (b) and (d) ranges from about 0.25 M to about 0.5 M.

5. The method according to claim 1, wherein said adsorbent particles in step (a) are agarose.

6. The method according to claim 1, wherein aminohexyl agarose is employed in step (c) as the adsorbent.

7. The method according to claim 6, wherein calcium chloride solution is employed as the elutant in steps (b) and (d), concentration of said calcium chloride solution ranging from about 0.25 M to about 0.5 M in step (b) and from about 0.25 M to about 0.5 M in step (d).

8. An improved immunoadsorbent for isolation and purification of VIII:C from VIII:C/VIII:RP comprising a monoclonal antibody specific to VIII:RP bound to solid particles.

9. The improved immunoadsorbent of claim 8, wherein said solid particles comprise a resin.

10. The improved immunoadsorbent of claim 9, wherein said resin comprises agarose.

11. The improved immunoadsorbent of claim 10, wherein said agarose is cross-linked agarose.

12. The improved immunoadsorbent of claim 11, wherein said immunoadsorbent has a coupling density of 3 to 4 g of monoclonal antibody per liter of agarose.

13. Highly purified and concentrated *human or porcine* VIII:C prepared in accordance with the method of claim 1.

14. Highly purified and concentrated *human or porcine* VIII:C prepared in accordance with the method of claim 6.

15. In a method for purifying Factor VIII procoagulant activity protein from plasma or concentrate, the improvement comprising the step of passing said plasma or concentrate through a chromatographic type column having adsorbent to which is bound monoclonal antibodies which is specific to VIII:RP and eluting the VIII-C therefrom.

16. The method according to claim 15, wherein said adsorbent is agarose and said elutant is a saline solution.

*17. A VIII:C of claim 13, wherein said VIII:C is human VIII:C.*

*18. A VIII:C of claim 14, wherein said VIII:C is human VIII:C.*

*19. An improved immunoadsorbent of claim 8 wherein said monoclonal antibody remains bound to VIII:RP during elution of VIII:C.*

*20. An improved immunoadsorbent of claim 19, wherein said elution is carried out with a saline solution.*

*21. An improved immunoadsorbent of claim 20 wherein said solution contains calcium ions.*

*22. An improved immunoadsorbent of claim 21, wherein said solution is calcium chloride.*

*23. An improved immunoadsorbent of claim 22, wherein the concentration of said calcium chloride is from 0.25 M to about 0.5 M.*

*24. A human VIII:C preparation having a potency in the range of 134 to 1172 units per ml, and being substantially free of VIII:RP.*

*25. A human VIII:C preparation of claim 24, wherein the VIII:C concentration is at least 160,000 fold purified relative to VIII:C in plasma.*

*26. A human VIII:C preparation of claim 24, wherein the ratio of VIII:C to VIII:RP is greater than 100,000 times the ratio in plasma.*

*27. A human VIII:C preparation of claim 24, wherein said VIII:C is isolated from VIII:C/VIII:RP and 90–100 percent of the VIII:RP has been removed.*

*28. A human VIII:C preparation having a specific activity greater than 2240 units/mg.*

*29. A human VIII:C preparation of claim 28 wherein the potency is in the range of 134 to 1172 units/ml.*

*30. An improved method of preparing Factor VIII procoagulant activity protein comprising the steps of*

*(a) adsorbing a VIII:C/VIII:RP complex from a plasma or commercial concentrate source onto a substrate to which is bound a monoclonal antibody specific to VIII:RP,*

*(b) eluting the VIII:C,*

*(c) adsorbing the VIII:C obtained in step (b) in another adsorption to concentrate and further purify same,*

*(d) eluting the adsorbed VIII:C, and*

*(e) recovering highly purified and concentrated VIII:C.*

*31. A method according to claim 30, wherein said substrate is a resin.*

*32. A method according to claim 30, wherein said substrate is comprised of particles.*

*33. An improved immunoadsorbent for isolation and purification of VIII:C from VIII:C/VIII:RP comprising a monoclonal antibody specific to VIII:RP bound to a substrate.*

*34. Highly purified and concentrated human or porcine VIII:C prepared in accordance with the method of claim 30.*

*35. In a method for purifying Factor VIII procoagulant activity protein from plasma or concentrate, the improvement comprising the step of passing said plasma or concentrate over a substrate to which is bound monoclonal antibodies which are specific to VIII:RP and eluting the VIII:C therefrom.*

*36. The method according to claim 35, wherein said substrate is agarose and said elutant is a saline solution.*

* * * * *